(12) United States Patent
Arai et al.

(10) Patent No.: US 10,667,738 B2
(45) Date of Patent: Jun. 2, 2020

(54) BRAIN ACTIVITY ESTIMATION DEVICE

(71) Applicants: DAIKIN INDUSTRIES, LTD., Osaka-shi, Osaka (JP); TOKYO INSTITUTE OF TECHNOLOGY, Meguro-ku, Tokyo (JP)

(72) Inventors: Junichiro Arai, Tokyo (JP); Yasunori Kotani, Tokyo (JP); Taro Tomatsu, Tokyo (JP); Yoshimi Ohgami, Tokyo (JP)

(73) Assignees: Daikin Industries, Ltd., Osaka (JP); Tokyo Institute of Technology, Tokyo (JP)

( * ) Notice: Subject to any disclaimer, the term of this patent is extended or adjusted under 35 U.S.C. 154(b) by 343 days.

(21) Appl. No.: 15/507,665

(22) PCT Filed: Aug. 28, 2015

(86) PCT No.: PCT/JP2015/074535
§ 371 (c)(1),
(2) Date: Feb. 28, 2017

(87) PCT Pub. No.: WO2016/035719
PCT Pub. Date: Mar. 10, 2016

(65) Prior Publication Data
US 2017/0281070 A1     Oct. 5, 2017

(30) Foreign Application Priority Data
Sep. 1, 2014   (JP) ................. 2014-177276

(51) Int. Cl.
*A61B 5/00*   (2006.01)
*A61B 5/16*   (2006.01)
*A61B 5/01*   (2006.01)

(52) U.S. Cl.
CPC .......... *A61B 5/4064* (2013.01); *A61B 5/0042* (2013.01); *A61B 5/0064* (2013.01);
(Continued)

(58) Field of Classification Search
CPC ............ A61B 2576/026; A61B 5/0042; A61B 5/0064; A61B 5/0075; A61B 5/015;
(Continued)

(56) References Cited

U.S. PATENT DOCUMENTS 8,328,420 B2   12/2012   Abreu
8,401,261 B2   3/2013   Pavlidis
(Continued)

FOREIGN PATENT DOCUMENTS

JP       8-252226 A       10/1996
JP    2012-34839 A        2/2012
(Continued)

OTHER PUBLICATIONS

Khan et al., Classifying Pretended and Evoked Facial Expressions of Positive and Negative Affective States using Infrared Measurement of Skin Temperature, Feb. 2009, ACM Transactions on Applied Perception.*
(Continued)

*Primary Examiner* — Joseph M Santos Rodriguez
(74) *Attorney, Agent, or Firm* — Global IP Counselors, LLP

(57) ABSTRACT

A brain activity estimation device includes a facial skin temperature acquisition element and a brain activity estimation element. The acquisition element detects a skin temperature of at least part of a human face, and acquires facial skin temperature data including detected temperature data and location data of a detection region in a time series manner. The estimation element estimates human brain activity based on the facial skin temperature data acquired.
(Continued)

The estimation element decomposes the facial skin temperature data into a plurality of components, extracts a component as a determination component, and determines whether the determination component is related to the human brain activity based on a presence or absence of a temperature change in a prescribed region of the human face.

14 Claims, 10 Drawing Sheets

(52) U.S. Cl.
CPC .......... *A61B 5/0075* (2013.01); *A61B 5/0077* (2013.01); *A61B 5/015* (2013.01); *A61B 5/165* (2013.01); *A61B 5/4884* (2013.01); *A61B 5/7246* (2013.01); *A61B 5/7264* (2013.01); *A61B 5/7278* (2013.01); *A61B 5/6814* (2013.01); *A61B 2576/026* (2013.01)

(58) Field of Classification Search
CPC ..... A61B 5/165; A61B 5/4064; A61B 5/4884; A61B 5/6814; A61B 5/7246; A61B 5/7264; A61B 5/7278
See application file for complete search history.

(56) References Cited

U.S. PATENT DOCUMENTS

| | | |
|---|---|---|
| 2005/0259849 A1 | 11/2005 | Pavlidis |
| 2009/0080730 A1 | 3/2009 | Pavlidis |
| 2010/0191124 A1 | 7/2010 | Prokoski |
| 2015/0065890 A1 | 3/2015 | Ishikawa et al. |

FOREIGN PATENT DOCUMENTS

| | | |
|---|---|---|
| JP | 2013-176406 A | 9/2013 |
| WO | 98/08431 A1 | 3/1998 |
| WO | 2013/168294 A1 | 11/2013 |

OTHER PUBLICATIONS

Nhan et al., Classifying Affective States Using Thermal Infrared Imaging of the Human Face, Apr. 2010, IEEE Transactions on Biomedical Engineering.*
International Search Report of corresponding PCT Application No. PCT/JP2015/074535 dated Nov. 17, 2015.
International Preliminary Report of corresponding PCT Application No. PCT/JP2015/074535 dated Aug. 28, 2015.
European Search Report of corresponding EP Application No. 15 837298.7 dated Feb. 1, 2018.

* cited by examiner

BRAIN ACTIVITY ESTIMATION DEVICE

CROSS-REFERENCE TO RELATED APPLICATIONS

This U.S. National stage application claims priority under 35 U.S.C. § 119(a) to Japanese Patent Application No. 2014-177276, filed in Japan on Sep. 1, 2014, the entire contents of which are hereby incorporated herein by reference.

TECHNICAL FIELD

The present invention relates to a brain activity estimation device for estimating a human brain activity.

BACKGROUND ART

There have been attempts in the prior art to estimate a human brain activity utilizing data that has been detected by functional magnetic resonance imaging (fMRI), near infrared spectroscopy (NIRS), or electroencephalography (EEG), such as is disclosed in Japanese Laid-open Patent Publication 2013-176406.

SUMMARY

Technical Problem

However, in cases in which electroencephalography or near infrared spectroscopy is adopted as the detection method, it is necessary to attach electrodes or probes, which require preparatory processing, to the test subject. In cases in which functional magnetic resonance imaging is adopted as the detection method, measurements can only be carried out in an MRI room. Specifically, in cases in which either electroencephalography, near infrared spectroscopy, or functional magnetic resonance imaging is adopted as the detection method, there are problems such as the complexity of the necessary operations to be performed in the preparatory stage, or limitations as to conditions during detection.

It is accordingly an object of the present invention to provide a brain activity estimation device with which a human brain activity can be estimated easily.

Solution to Problem

The brain activity estimation device according to a first aspect of the present invention is equipped with a facial skin temperature acquisition element (means), and a brain activity estimation element (means). The facial skin temperature acquisition means detects the skin temperature of at least part of a person's face. The facial skin temperature acquisition means acquires facial skin temperature data that includes detected temperature data and location data of the detection region thereof in a time series manner. The brain activity estimation means estimates the human brain activity on the basis of facial skin temperature data acquired by the facial skin temperature acquisition means. The brain activity estimation means also decomposes the facial skin temperature data into a plurality of components by singular value decomposition, principal component analysis, or independent component analysis. The brain activity estimation means also extracts a component as a determination component from among the plurality of components. The component has the amplitude of the component waveform thereof is correlated to a changes at a time when the brain is at rest and a time when the brain is stimulated. The brain activity estimation means also determines whether the determination component is related to the human brain activity on the basis of the presence or absence of a temperature change in a prescribed region of a human face.

With the brain activity estimation device according to the first aspect of the present invention, a human brain activity is estimated on the basis of a time series of facial skin temperature data acquired by the facial skin temperature acquisition means. For this reason, with this brain activity estimation device, a human brain activity can be estimated on the basis of facial skin temperature without attaching sensors such as brain wave electrodes or probes which require processing prior to attachment. Consequently, a human brain activity can be estimated more easily than in cases in which conventional detection methods, such as electroencephalography, functional magnetic resonance imaging, or near infrared spectroscopy is utilized.

A brain activity estimation device according to a second aspect of the present invention is the brain activity estimation device according to the first aspect of the present invention wherein the facial skin temperature data includes data recorded during a period in which the person is presented with a brain function-stimulating task. The brain activity estimation means designates a period during which a person is not being presented with the brain function-stimulating task as a time when the brain is at rest. The brain activity estimation means designates a period during which the person is being presented with the brain function-stimulating task as a time when the brain is being stimulated. The brain activity estimation means then evaluates whether a correlation exists in the plurality of components. The brain activity estimation means further extracts a component evaluated as having the correlation from among the plurality of components, as the determination component. Therefore, with this brain activity estimation device, circumstances in which the human brain is activated or placed at rest are actually created by presenting or not presenting the individual with a brain function-stimulating task, and the correlation is evaluated on the basis thereof, and a determination component is extracted. It is therefore possible to reduce the risk that a component having weak correlation to a human brain activity will be selected as an extraction component from among a plurality of components.

A brain activity estimation device according to a third aspect of the present invention is the brain activity estimation device according to the first or second aspect of the present invention wherein the brain activity estimation means creates facial skin temperature data in which the temperature data included in the facial skin temperature data acquired at each of prescribed points in time is converted to relative temperature data. Then, for each set of the acquired facial skin temperature data and set of the created facial skin temperature data, the brain activity estimation means decomposes the data into a plurality of components by singular value decomposition, principal component analysis, or independent component analysis.

There are instances in which the skin temperature of the face varies due to a human face being contacted by cold or hot air from an air conditioner, by sunlight, or the like, so that the detected skin temperature of the face varies. In such cases, changes in facial skin temperature due to extrinsic factors unrelated to brain activity (noise) can get mixed into the facial skin temperature data.

With the brain activity estimation device according to the third aspect of the present invention, facial skin temperature data converted to relative temperature data is created from facial skin temperature data acquired at each of prescribed points in time according to temperature data detected by the facial skin temperature acquisition means. Then, in addition to the facial skin temperature data according to detected temperature data, the facial skin temperature data that has been converted to relative temperature data is decomposed into a plurality of components by singular value decomposition, principal component analysis, or independent component analysis. Specifically, with this brain activity estimation device, by creating facial skin temperature data that has been converted to relative temperature data, it is possible to track relative changes in skin temperature of the face at prescribed points in time. Therefore, changes in facial skin temperature due to extrinsic factors unrelated to brain activity can be detected.

A brain activity estimation device according to a fourth aspect of the present invention is the brain activity estimation device according to any of the first to third aspects of the present invention wherein the facial skin temperature acquisition means is an infrared thermography device. With this brain activity estimation device, the skin temperature of the face is detected by the infrared thermography device, and therefore the burden imposed on the person targeted for detection can be made less than when sensors or the like are attached to the face to detect the skin temperature of the face.

A brain activity estimation device according to a fifth aspect of the present invention is the brain activity estimation device according to any of the first to fourth aspects of the present invention wherein the prescribed region is a paranasal sinus peripheral region and/or a forehead.

The brain has a mechanism called the selective brain cooling system, whereby the brain is cooled independently of body temperature. It is known that the selective brain cooling system removes heat produced by brain activity using the forehead and the paranasal sinus peripheral region.

With a brain activity estimation device according to a fifth aspect of the present invention, for a determination component having a correlation to a change occurring when the brain is at rest or when the brain is stimulated, a determination is made as to whether the component is related to a human brain activity, on the basis of whether there is a temperature change of the paranasal sinus peripheral region and/or forehead. In so doing, a component that is associated with a human brain activity can be accurately identified.

A brain activity estimation method according to a sixth aspect of the present invention is provided with a facial skin temperature acquisition step, and a brain activity estimation step. In the facial skin temperature acquisition step, skin temperature in at least part of a person's face is detected, and facial skin temperature data that includes detected temperature data and location data of the detection region is acquired in a time series manner. In the brain activity estimation step, the human brain activity is estimated on the basis of the facial skin temperature data acquired in the facial skin temperature acquisition step. The brain activity estimation step also includes a decomposition step, and extraction step, and a determination step. In the decomposition step, the facial skin temperature data is decomposed into a plurality of components by singular value decomposition, principal component analysis, or independent component analysis. In the extraction step there is extracted, as a determination component from among the plurality of components that were decomposed in the decomposition step, a component for which the amplitude of the component waveform thereof is correlated to a change at a time when the brain is at rest and a time when the brain is stimulated. In the determination step, whether the determination component that was extracted in the extraction step is related to the person's brain activity is determined on the basis of the presence or absence of a temperature change in a prescribed region of the human face.

In the brain activity estimation method according to the sixth embodiment of the present invention, a human brain activity is estimated on the basis of a time series of facial skin temperature data acquired in the facial skin temperature acquisition step. Therefore, a human brain activity can be estimated more easily, as compared with cases in which prior-art detection methods, such as electroencephalography, functional magnetic resonance imaging procedure, or near infrared spectroscopy is utilized.

Advantageous Effects of Invention

With the brain activity estimation device according to the first aspect of the present invention, a human brain activity can be estimated easily.

With the brain activity estimation device according to the second aspect of the present invention, it is possible to reduce the risk that a component having weak correlation to a human brain activity will be selected as an extraction component from among a plurality of components.

With the brain activity estimation device according to the third aspect of the present invention, changes in facial skin temperature due to extrinsic factors unrelated to brain activity can be detected.

With the brain activity estimation device according to the fourth aspect of the present invention, the burden imposed on the person targeted for detection can be reduced.

With the brain activity estimation device according to the fifth aspect of the present invention, a component that is associated with a human brain activity can be accurately identified.

With the brain activity estimation method according to the sixth aspect of the present invention, a human brain activity can be estimated easily.

DESCRIPTION OF EMBODIMENTS

Figure 1A:
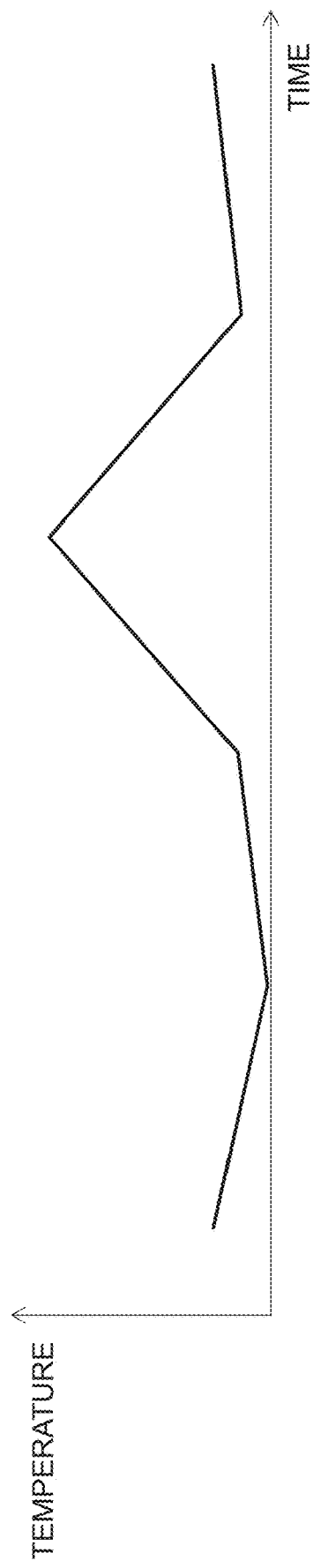
FIG. 1 shows an example of a relationship between temperature and time in facial temperature data.

Before describing the embodiments of the present invention, the discovery made by the inventors that served as an important foundation for the inventors to contrive the present invention will be described first.

(1) Summary of Discovery Made by the Inventors

It is known that a person's intellectual activity (cognitive activity and the like) and emotional activity (activity such as pleasure/displeasure) is reflected in a human brain activity. Attempts to estimate a human brain activity have been made in the past, but in most cases, data detected by any method selected from electroencephalography, functional magnetic resonance imaging, and near infrared spectroscopy was utilized.

In cases in which, for example, electroencephalography is selected as a detection method, it is necessary to attach brain wave electrodes to the test subject. Since it is moreover necessary to reduce resistance between the skin and the electrodes when the brain wave electrodes are worn, a procedure such as a process to abrade the skin, or an application of a paste to the electrodes is needed to be carried out. In cases in which functional magnetic resonance imaging is selected, because it is impossible to take measurements at locations other than an MRI room, there are restrictions as to the measurement conditions, such as the fact that metals cannot be brought into the measurement room. In a case where near infrared spectroscopy is selected, it is necessary to attach a probe to the test subject, but wearing the probe for an extended period may cause the test subject to experience pain, and there may be instances in which detection cannot take place accurately due to a state of contact between the probe and the test subject's hair. In this way, when conventional detection methods are used in order to measure a human brain activity, a significant burden is imposed on the test subject, preparatory processes during attachment of the brain wave electrodes or probe are needed, or the measurement conditions are limited, and other burdens are imposed.

Accordingly, there is a need to develop a means by which the burden on test subjects can be reduced, and a human brain activity can be estimated easily.

The brain has a mechanism called the selective brain cooling system, whereby the brain is cooled independently of body temperature. It is known that the selective brain cooling system removes heat produced by brain activity using the forehead and the paranasal sinus peripheral region. Thus, changes in facial skin temperature accompanying brain activity will appear in the forehead and/or paranasal sinus peripheral region (the glabella and paranasal peripheral region).

The inventors conceived of the idea that, if changes in the skin temperature of a person's face due to this selective brain cooling system could be tracked, brain activity could be measured without carrying out brain wave measurements or the like. Moreover, the data of the skin temperature of a human face can be acquired in a time series manner without attaching sensors that require a preparatory process.

However, it is known that the skin temperature of a person's face changes due to the effects of various factors such as the outside temperature and/or autonomic nervous activity and the like. For this reason, if brain activity is estimated on the basis of facial skin temperature, it is extremely difficult to decide whether detected facial skin temperature reflects only brain activity.

As a result of painstaking research, the inventors discovered that a component that indicates changes in skin temperature reflecting brain activity can be identified by detecting the skin temperature of the face, and decomposing facial skin temperature data that includes detected temperature data and location data (coordinate data) for the detected regions into a plurality of components by using singular value decomposition, principal component analysis, or independent component analysis, and analyzing the decomposed plurality of components by using the selective brain cooling system. Specifically, it was ascertained that, in cases in which it is attempted to estimate a human brain activity on the basis of facial temperature data, it is effective to decompose the facial skin temperature data into a plurality of components by singular value decomposition, principal component analysis, or independent component analysis. By focusing upon this feature, the inventors arrived at the present invention, with which a human brain activity can be estimated without attaching sensors that require preparatory processing, such as brain wave electrodes or probes.

Figure 1B:
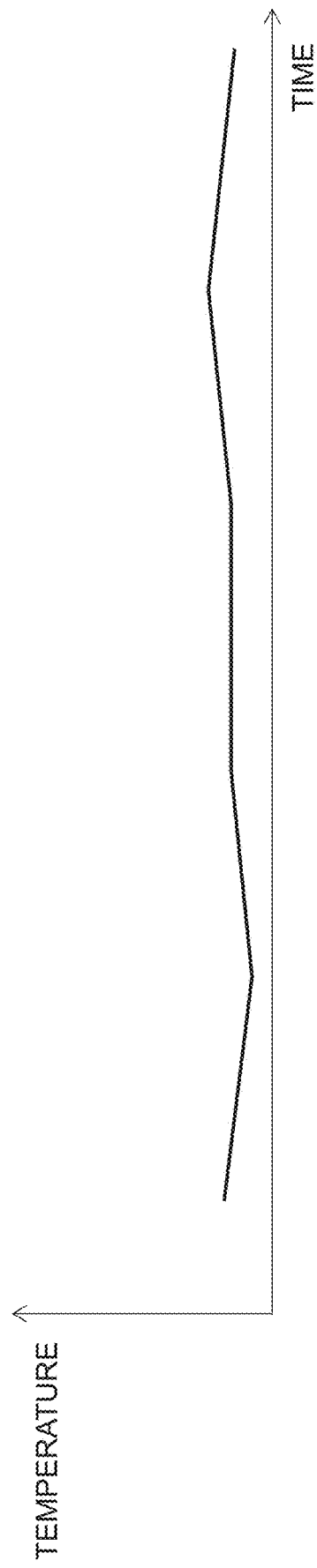

(2) Facial Skin Temperature Data Acquisition Method, and Facial Skin Temperature Data Analysis Method FIG. 1 (a) shows an example of a relationship between temperature and time in acquired facial temperature data. FIG. 1 (b) shows an example of a relationship between temperature and time in facial skin temperature data shown in FIG. 1(a) that has been created by conversion of temperature data included in facial skin temperature data acquired at each of prescribed points in time, to relative temperature data.

Next, a facial skin temperature data acquisition method and a facial skin temperature data analysis method employed when inventors made the aforementioned discovery shall be described.

In the present test, facial skin temperature data was acquired from six test subjects. Specifically, the test subjects were seated in chairs arranged in an artificial climate room maintained at a room temperature of 25° C., and facial skin temperature data was acquired from the test subjects' entire face using an infrared thermography device. An infrared thermography device is a device that makes it possible for infrared emission energy emanating from a target to be detected by an infrared camera, the detected infrared emission energy to be converted to the surface temperature of the target (in the present embodiment, degrees Celsius), and a temperature distribution thereof to be displayed and cumulated in the form of facial skin temperature data (e.g., image data representing a temperature distribution). In the present test, an R300 made by NEC Avio Infrared Technologies Co. Ltd. was used as the infrared thermography device. The infrared camera was arranged at a location to the front of the test subject, and 1.5 m away from the test subject. The facial skin temperature data was acquired for a 30-minute period.

In the present test, during the interval that the facial skin temperature data was being acquired, the test subjects were presented with brain function-stimulating tasks. In so doing, facial skin temperature data with the brain at rest, and facial skin temperature data while the brain is stimulated, were acquired.

As brain function-stimulating tasks there may be cited psychological works whereby, on the basis of video images shown on a display screen or the like, test subjects recognize calculations, or numbers, shapes, and colors, memorize symbols, characters or words, or the like. In the present test, "doing mental multiplication" was selected as the brain function-stimulating task; test subjects being assigned the work of calculating numbers shown in paper calculation format on a display device, and inputting the answers on a keyboard. In the present test, the test subjects were presented with the brain function-stimulating tasks for a continuous 10-minute period after 5 minutes from the start of acquisition of the facial skin temperature data.

For the analysis of the facial skin temperature data, singular value decomposition (SVD) was carried out using MATLAB (registered trademark)'s SVD (Singular Value Decomposition) as the analysis tool on the acquired facial skin temperature data. In singular value decomposition, the analysis was carried out while targeting all of the facial skin temperature data acquired in the form of a time series (30 minutes' worth of data), designating time data taken every 30 seconds (60 time points in 30 minutes) as factors, and designating the facial skin temperature data (240×320 pixels) for the periods (30 seconds) as measures. Then, through singular value decomposition, the facial skin temperature data X was decomposed into a plurality of components, and a temporal distribution V of the respective components, a spatial distribution U, and a singular value S indicating the magnitude of the components were calculated. These relationships are represented by the following equation. V' is a matrix in which the rows and columns of V have been transposed.

$$X=(U*S)*V'$$ [Mathematical Formula 1]

The temporal distribution V and the spatial distribution U of the components derived through singular value decomposition were plotted on a graph, and a component waveform chart and temperature distribution chart of the components were created.

Further, the created component waveform chart and temperature distribution chart of the components were analyzed to identify components that are indicative of changes of skin temperature reflective of brain activity.

The component waveform chart of the components was analyzed for any correlation between the amplitude of the component waveform thereof, and instances when the brain was at rest or stimulated. Specifically, an evaluation was conducted on whether a correlation existed between the amplitude indicated by the component waveform chart of the components, and the brain-at-rest intervals/brain-stimulation intervals. In the present test, among the intervals in which facial skin temperature data was acquired, a 5-minute interval extending from the data acquisition start point and up to a point in time after 5 minutes had passed, and a 15-minute interval extending from point in time after 15 minutes had passed since the data acquisition start point and up to the data acquisition end point, which were intervals in which the test subjects were not presented with brain activity-stimulating tasks, were designated as times when the brain was at rest. A 10-minute period extending from a point in time occurring after 5 minutes had elapsed since the data acquisition start point, up to a point in time after 10 minutes had elapsed, which was the interval in which the test subjects were presented with brain activity-stimulating tasks, was designated as time when the brain was being stimulated. An evaluation was made as to the presence or absence of correlation between the amplitude indicated by the component waveform chart of the components, and times when the brain was at rest or times when the brain was stimulated. A statistical correlation analysis was carried out as to the presence or absence of correlation, and a correlation was determined to exist in which the significance level (a) was 0.05 or less.

The temperature distribution chart of the components was analyzed as to the presence or absence of temperature changes in prescribed regions of the face. Specifically, the temperature distribution chart of the components was evaluated as to whether there were temperature changes in the paranasal sinus peripheral region and the forehead. The criterion for assessing the presence or absence of temperature changes in the paranasal sinus peripheral region and the forehead in the temperature distribution chart was the presence or absence of temperature changes as determined by visual inspection. Alternatively, whether there were temperature changes such that the temperature of the paranasal sinus peripheral region and the forehead differs by at least one standard deviation (SD) from the average temperature of all of the measurement data was used as the criterion.

The polarity (plus or minus) of the facial skin temperature data X is determined by relationships among values of the spatial distribution U, the singular value S, and the temporal distribution V; accordingly, there are instances in which polarity appears reversed in the component waveform chart and the temperature distribution chart of the components. For this reason, it was decided to exclude polarity from the evaluation, when evaluating the component waveform chart and the temperature distribution chart.

As stated previously, with this infrared thermography device, infrared emission energy detected from a target is converted to temperature, and the temperature distribution thereof is used as facial skin temperature data in the present embodiment. In cases in which facial skin temperature is acquired using an infrared thermography device from a human target, facial skin temperature data representing various temperature changes unrelated to brain activity ("noise") such as facial movements and/or autonomic nervous activity, may also be acquired (see FIG. 1 (a)). In order to detect such temperature changes unrelated to brain activity, relative facial skin temperature data in which a value of 0 is adopted to the overall average value of the temperature data included in facial skin temperature data captured every 30 seconds was created. Then, singular value decomposition was carried out using MATLAB (registered trademark)'s SVD as the analysis tool on the created facial skin temperature data. A component waveform chart and a temperature distribution chart of the components according to the singular value S were created. Then, an analysis was conducted to identify a component that indicates changes in skin temperature reflecting brain activity.

For convenience in the description that follows, facial skin temperature data acquired with the infrared thermography device shall be termed "facial skin temperature data corresponding to temperature conversion data," and relative facial skin temperature data in which a value of 0 is adopted to the overall average value of the temperature data included in facial skin temperature data that is associated with temperature conversion data captured at each of prescribed points in time (in the present test, every 30 seconds) shall be termed "facial skin temperature data corresponding to relative temperature conversion data."

To the one of the six test subjects who was conducted a detection of facial skin temperature with the infrared thermography device; additionally, electrodes were connected onto the test subject's scalp, the brain waves were measured, and an evaluation was made regarding correlation between the amplitude of β waves (brain waves of 14-30 Hz frequency), which are known as waveforms that appear at times of arousal or at times of tensed feeling, and the amplitude of the component waveform chart. Brain wave measurements were carried out on the basis of the International 10-20 system, placing the electrodes in six regions (F3, F4, C3, C4, Cz, and Pz).

It is conceivable that during the time that a test subject is being presented with a brain function-stimulating task, the test subject's head might move up and down. Should this happen, the position of the test subject's face with respect to the infrared camera will change. In order to verify whether this change in the position of the face affects change in skin temperature, a comparative experiment was carried out on one test subject. In the comparative experiment for verifying the effects of movement of the test subject during acquisition of facial skin temperature data, facial skin temperature data of the test subject was acquired using the infrared thermography device in the same manner as in the aforedescribed test, but the test subject was made to perform a work involving pressing a keyboard at random timing during periods in which the subject was not being presented with a brain function-stimulating task (i.e. when the brain was at rest). Singular value decomposition using MATLAB (registered trademark)'s SVD as the analysis tool was carried out on the facial skin temperature data corresponding to temperature conversion data and the facial skin temperature data corresponding to relative temperature conversion data obtained by this comparative experiment. A component waveform chart and a temperature distribution chart of the components corresponding to the singular value S were created. Then, an analysis was performed to identify a component that indicates changes in skin temperature reflecting brain activity.

(3) Results of an Analysis of Facial Skin Temperature Data

Figure 2A:
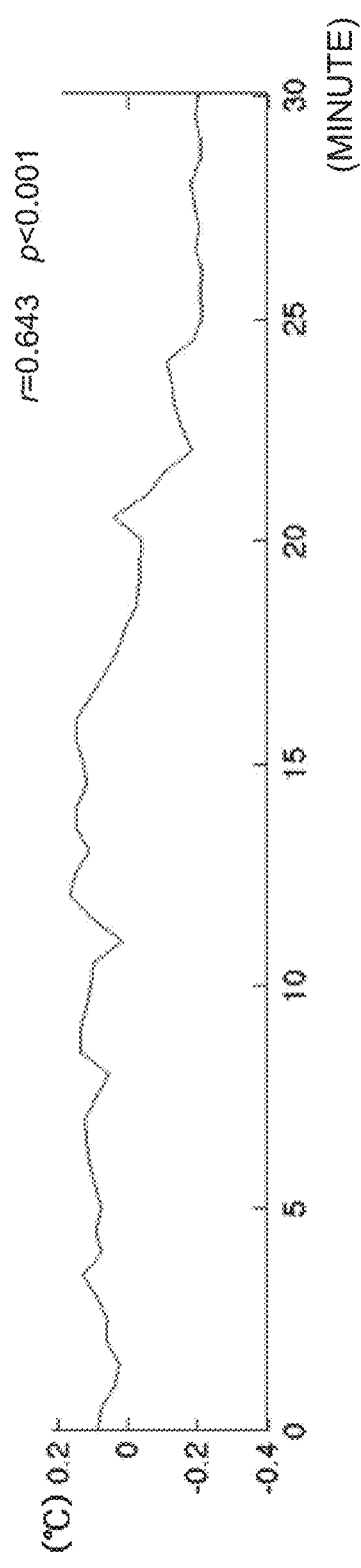
FIG. 2 shows some of the results of an analysis of facial skin temperature data corresponding to temperature conversion data.
Figure 2B:
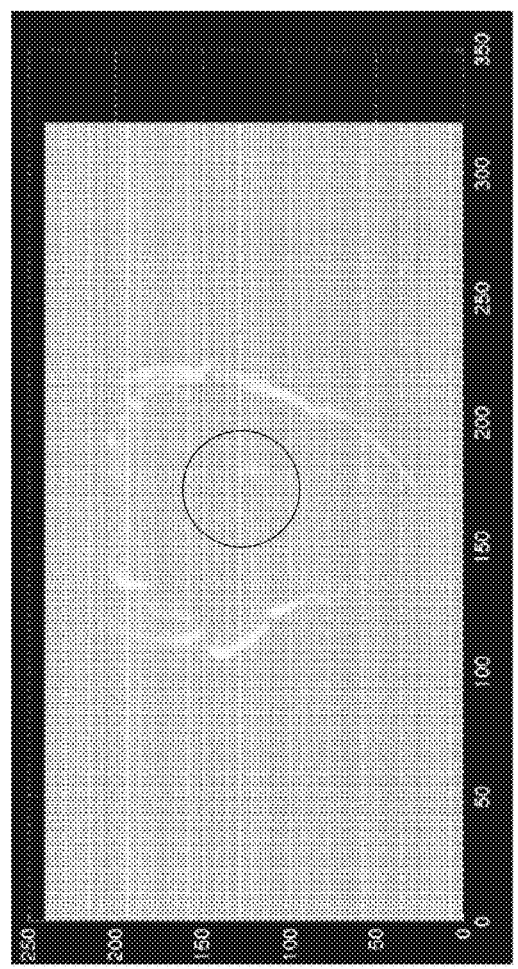
Figure 3A:
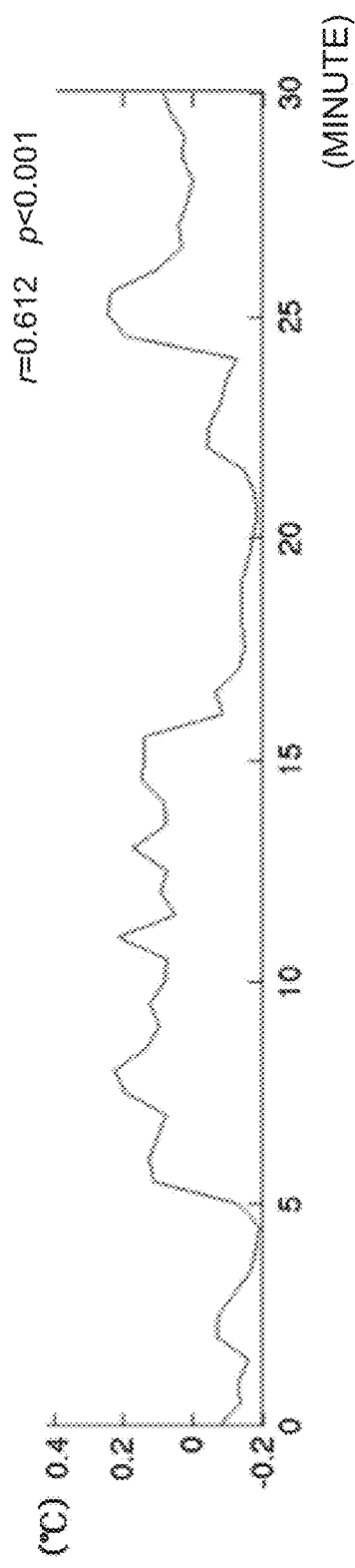
FIG. 3 shows some of the results of an analysis of facial skin temperature data corresponding to temperature conversion data.
Figure 3B:
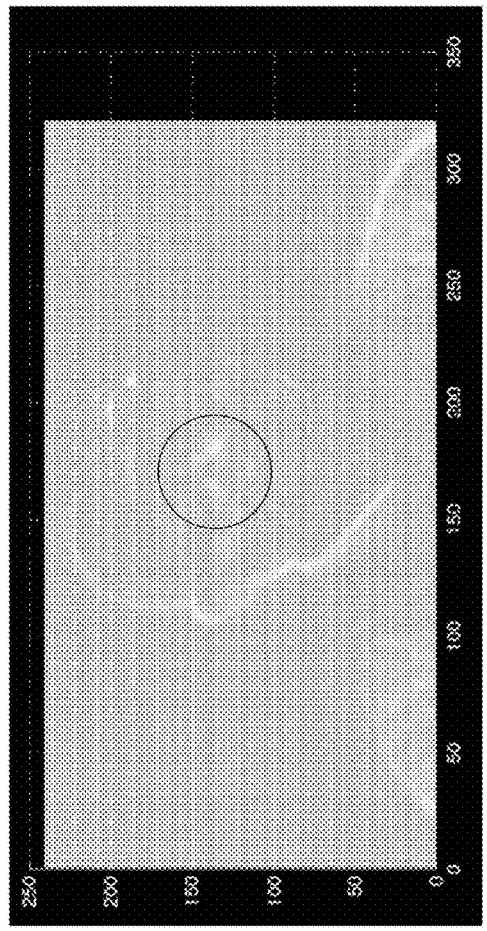
Figure 4A:
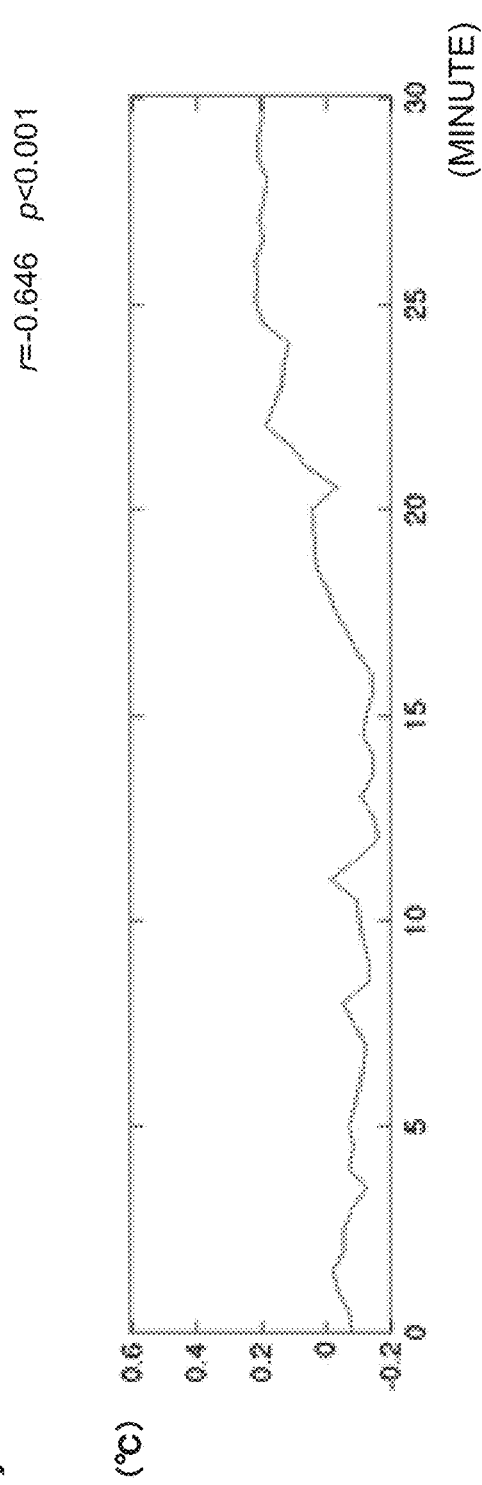
FIG. 4 shows some of the results of an analysis of facial skin temperature data corresponding to relative temperature conversion data.
Figure 4B:
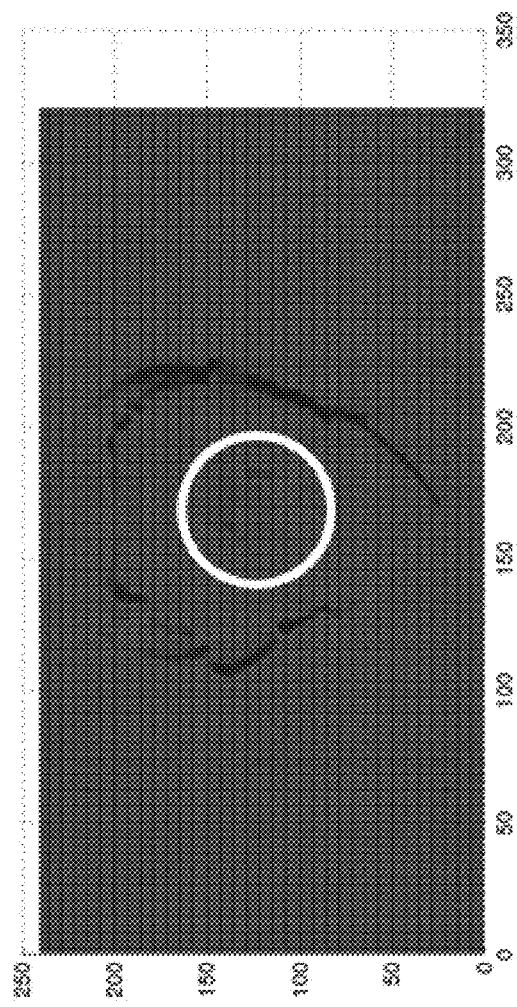
Figure 5A:
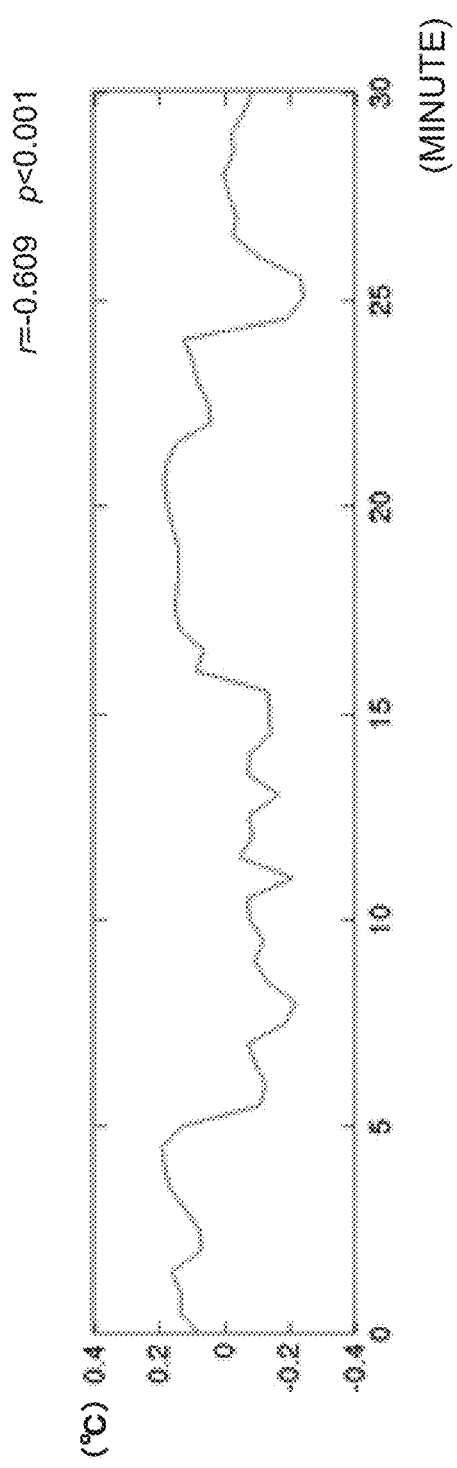
FIG. 5 shows some of the results of an analysis of facial skin temperature data corresponding to relative temperature conversion data.
Figure 5B:
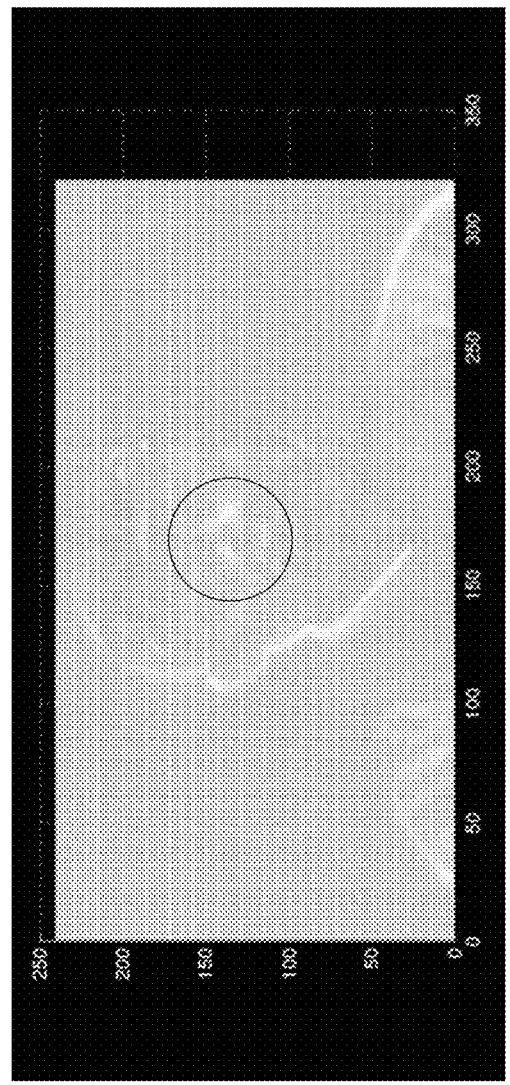
Figure 6:
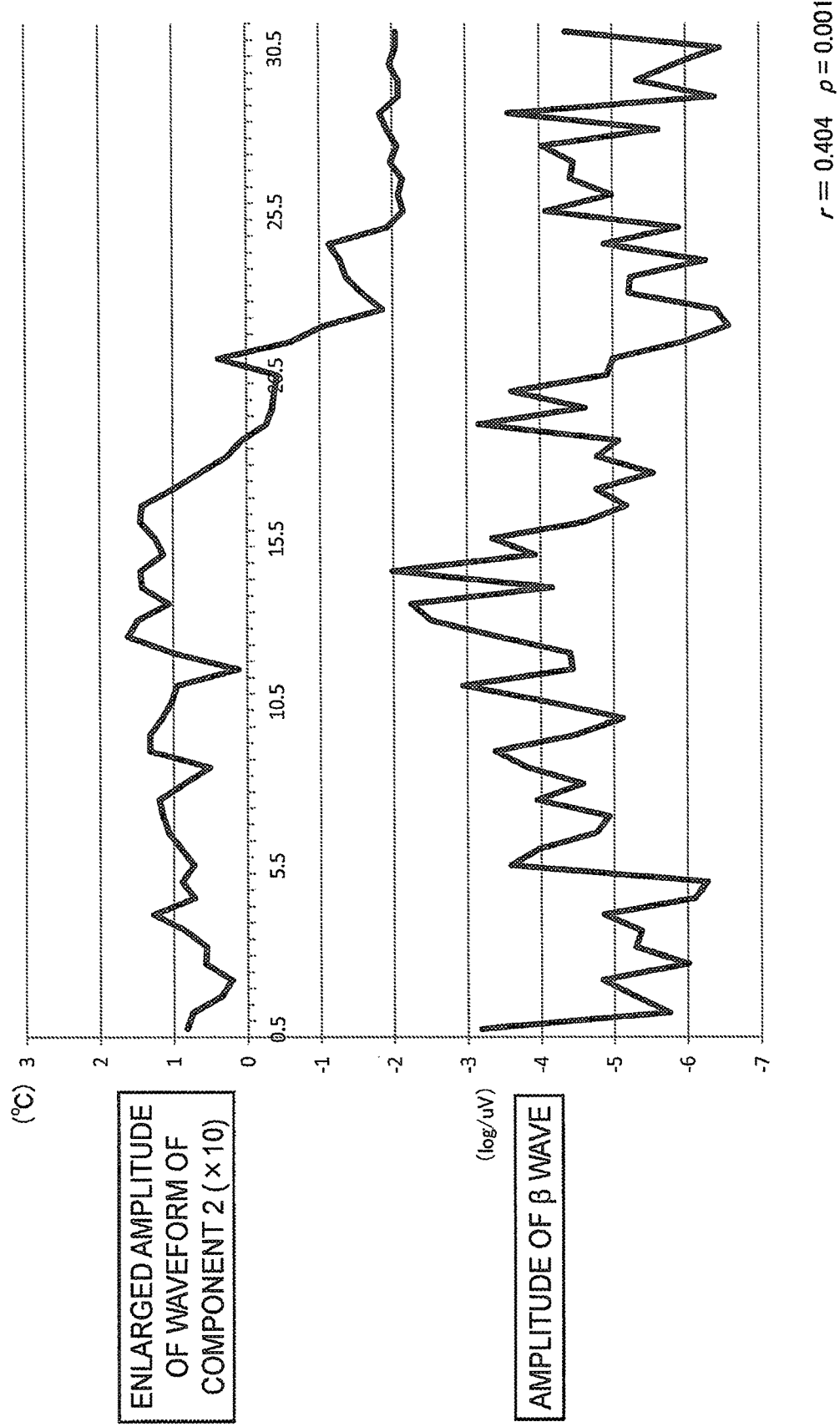
FIG. 6 shows the amplitude of a waveform of a component 2, and the amplitude of a β wave among measured brain waves.
Figure 7:
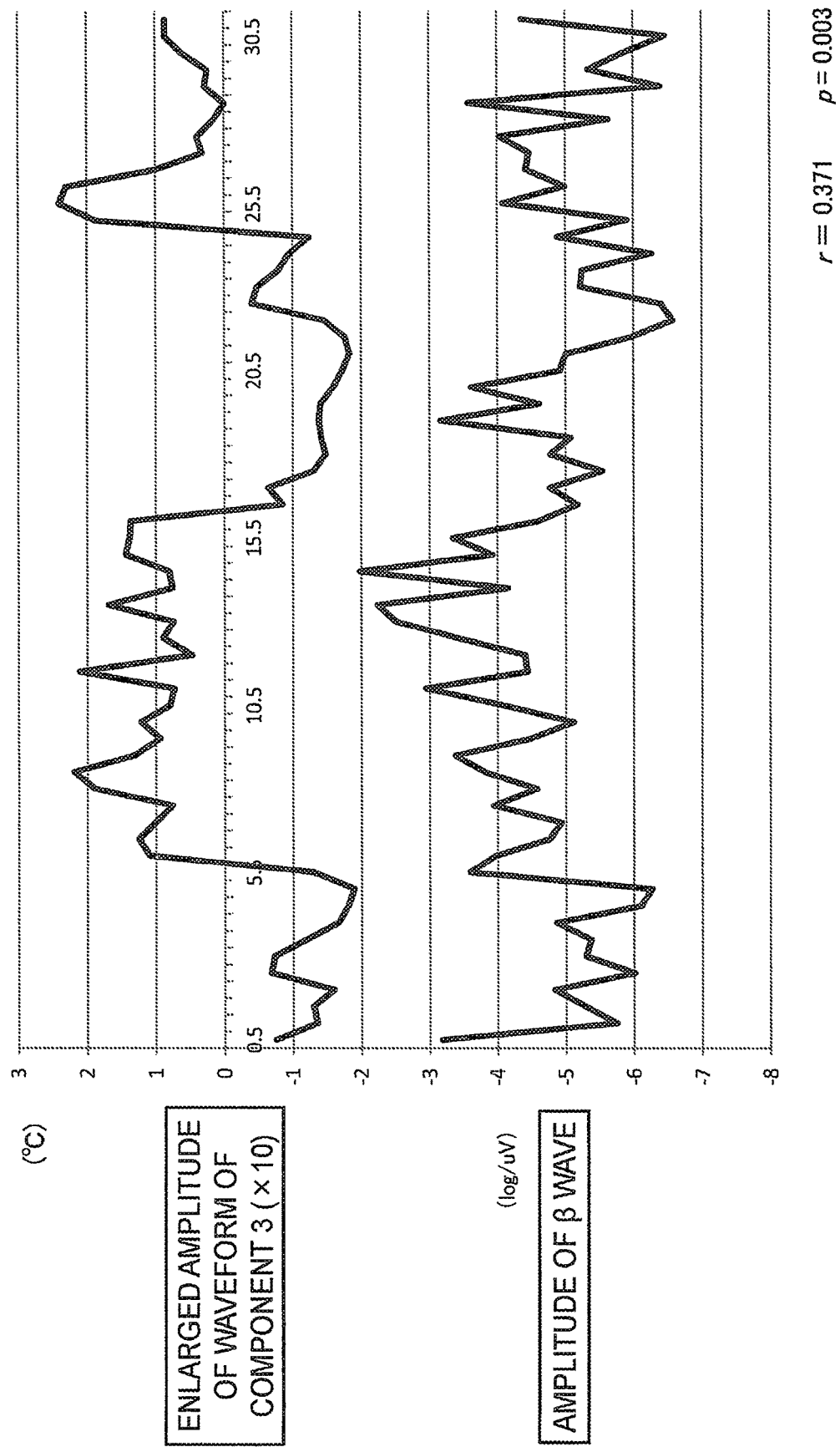
FIG. 7 shows the amplitude of a waveform of a component 3, and the amplitude of a β wave among measured brain waves.
Figure 8A:
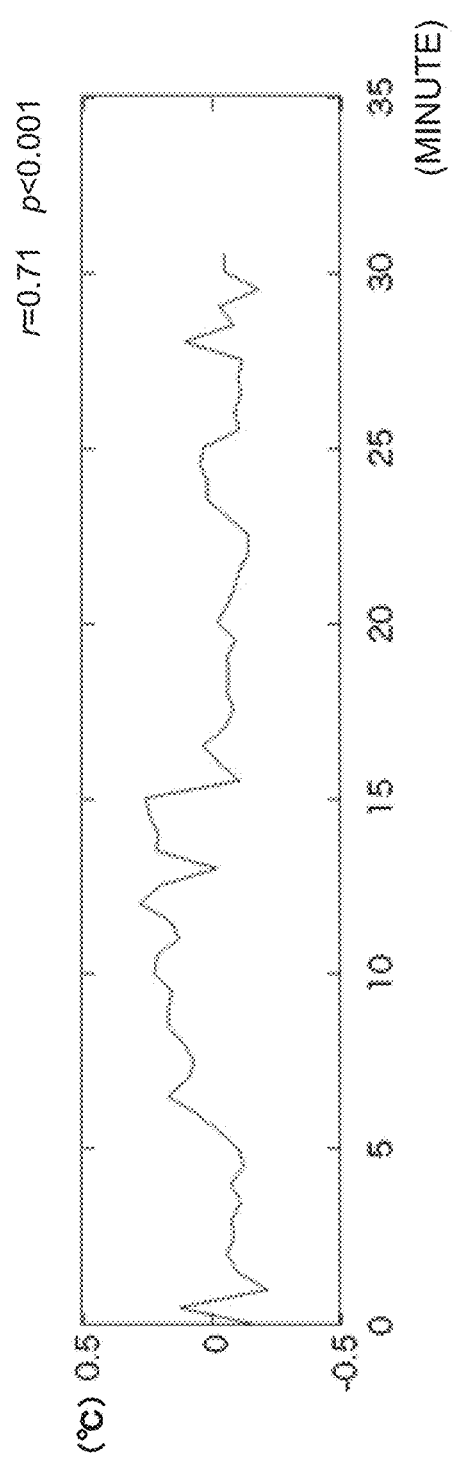
FIG. 8 shows some of the results of an analysis of facial skin temperature data obtained in a control experiment.
Figure 8B:
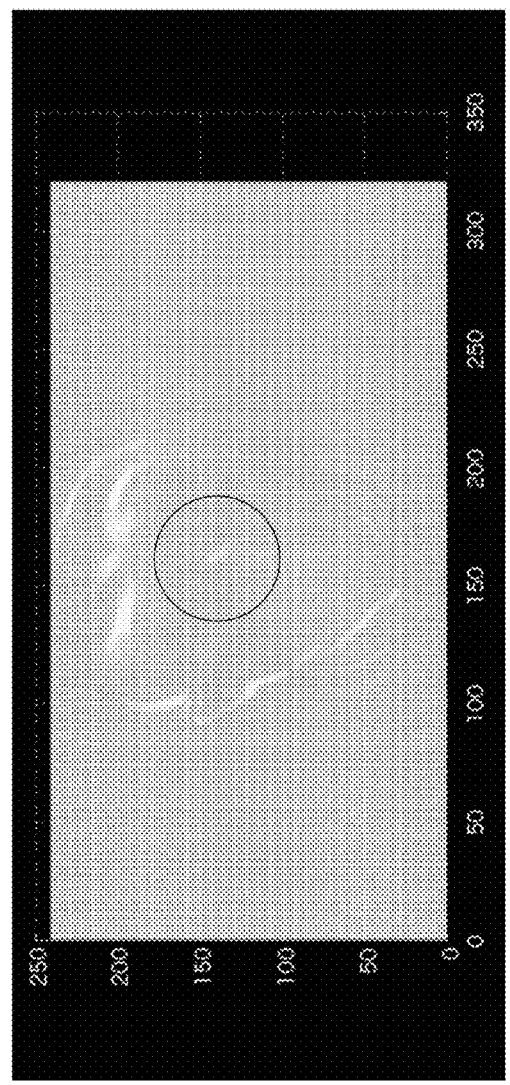

FIGS. 2 and 3 show some of the results of an analysis of facial skin temperature data corresponding to temperature conversion data. FIG. 2 (a) shows a component waveform chart of a component 2 of a test subject 1. FIG. 2 (b) shows a temperature distribution chart of a component 2 of a test subject 1. FIG. 3 (a) shows a component waveform chart of a component 3 of the test subject 1. FIG. 3 (b) shows a temperature distribution chart of a component 3 of the test subject 1. FIGS. 4 and 5 show some of the results of an analysis of facial skin temperature data corresponding to relative temperature conversion data. FIG. 4 (a) shows a component waveform chart of the component 2 of the test subject 1. FIG. 4 (b) shows a temperature distribution chart of the component 2 of the test subject 1. FIG. 5 (a) shows a component waveform chart of the component 3 of the test subject 1. FIG. 5 (b) shows a temperature distribution chart of the component 3 of the test subject 1. FIG. 6 and FIG. 7 show relationships between component waveform amplitude and brain waves. FIG. 6 shows the amplitude of the component waveform chart of the component 2 of the test subject 1, and the amplitude of the β wave among the measured brain waves. FIG. 7 shows the amplitude of the component waveform chart of the component 3 of the test subject 1, and the amplitude of the β wave among the measured brain waves. FIG. 8 shows some of the results of an analysis of facial skin temperature data obtained in a comparative test. FIG. 8 (a) shows a component waveform chart of the component 3. FIG. 8 (b) shows a temperature distribution chart of the component 3.

Table 1 shows results of an analysis of facial skin temperature data for each test subject.

From the results obtained by analysis of the aforedescribed facial skin temperature data, it was found that, among a plurality of components obtained by decomposing a time series of facial skin temperature data by singular value decomposition, component 2 and/or component 3 had a significant correlation to a human brain activity.

TABLE 1

| Test subject | Correlation in data based on temperature conversion data | | Correlation in data based on relative conversion data | |
|---|---|---|---|---|
| | Component waveform | Temperature distribution | Component waveform | Temperature distribution |
| Test subject 1 | Components 2, 3 | Components 2, 3 | Components 2, 3 | Components 2, 3 |
| Test subject 2 | Component 3 | Component 3 | Component 3 | Component 3 |
| Test subject 3 | Components 1, 2, 3 | Components 2, 3 | Components 2, 3 | Components 2, 3 |
| Test subject 4 | Components 2, 3 | Components 2, 3 | Components 2, 3 | Components 2, 3 |
| Test subject 5 | Components 2, 3 | Components 2, 3 | Components 2, 3 | Components 2, 3 |
| Test subject 6 | Components 2, 5 | Components 2, 5 | Components 2, 5 | Components 2, 5 |

As shown in FIGS. 6 and 7, from the results of brain wave analysis, it was confirmed that there is significant correlation between the amplitude of the component waveforms of component 2 and component 3, and the amplitude of the β wave of brain waves.

Further, in the comparative experiment, even under conditions in which test subjects were moving while the facial skin temperature data was being acquired, there was a significant correlation between component 3 and a human brain activity (see FIG. 8). From these findings it was concluded that, among the plurality of components, component 3 was unaffected by movement of the test subject during acquisition of facial skin temperature data.

From these results, the inventors made the following discovery.

As a result of having used singular value decomposition to decompose a time series of facial skin temperature data acquired from test subjects into a plurality of components, and analyzing the decomposed components, it was concluded that component 3 among the plurality of components is related to brain activity. Specifically, it was ascertained that by using singular value decomposition to decompose a time series of facial skin temperature data, extracting from among the plurality of decomposed components, those components having correlation to brain rest/stimulation, and carrying out an analysis of the extracted components using the selective brain cooling mechanism, it is possible to identify a component among a plurality of components that indicates changes in skin temperature reflecting brain activity. From this, the inventors made the discovery that brain activity can be estimated on the basis of a human facial skin temperature.

(4) Brain Activity Estimation Device

Next, the brain activity estimation device according to one embodiment of the present invention, which was perfected by the inventors on the basis of the discovery described above, shall be described. The brain activity estimation device according to the present invention is not limited to the following embodiment; various appropriate modifications are possible without departing from the scope of the invention.

Figure 9:
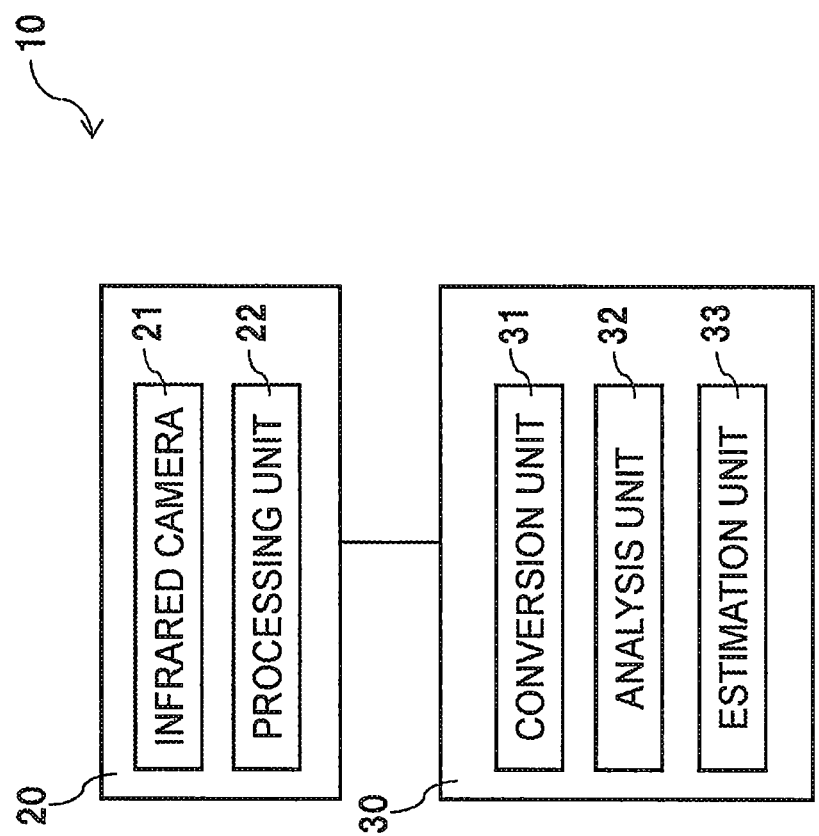
FIG. 9 illustrates a simplified diagram of a brain activity estimation device according to an embodiment of the present invention.
Figure 10:
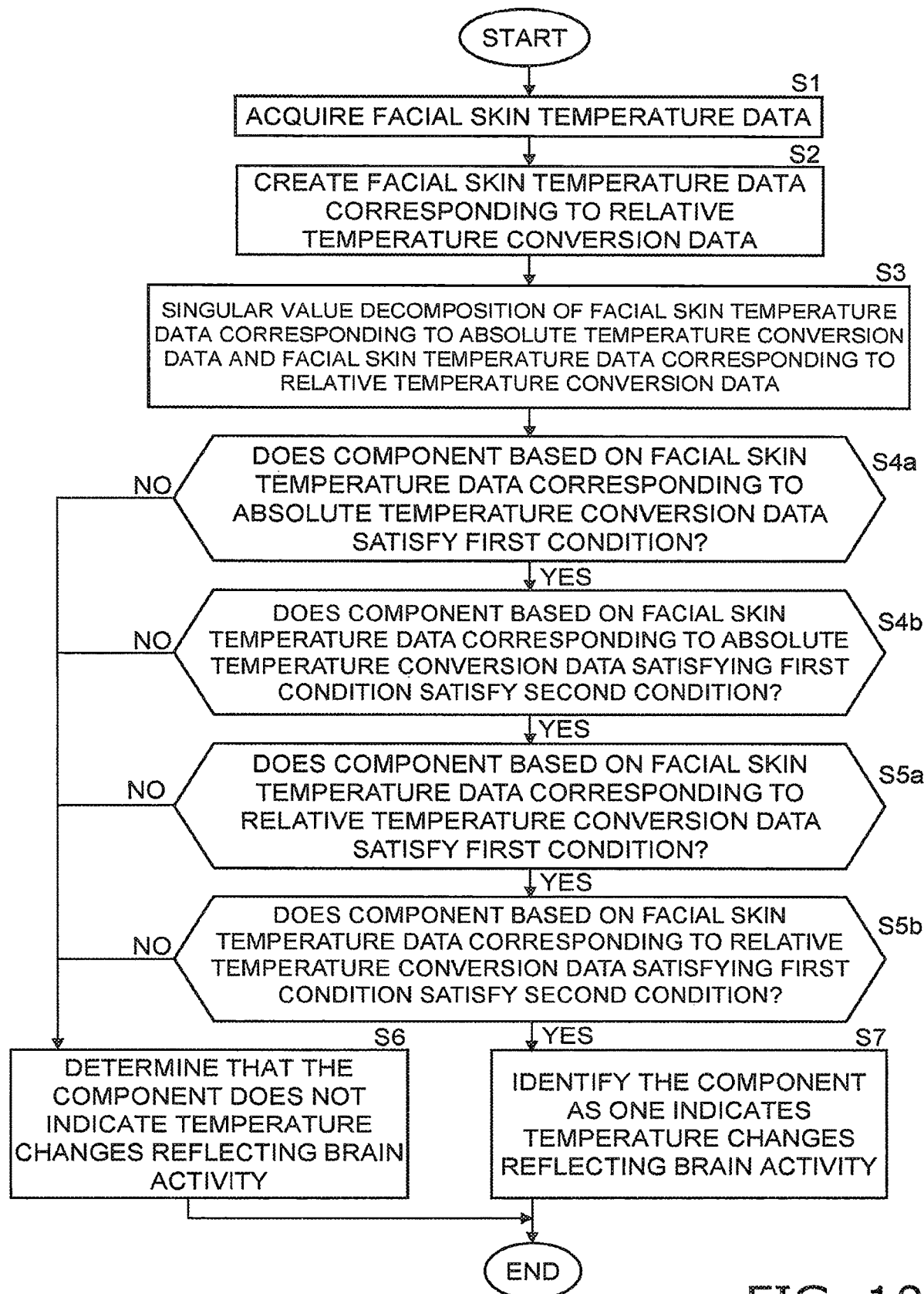
FIG. 10 illustrates a flowchart showing the flow of a process during identification of a component indicating a change in skin temperature that reflects brain function in a brain activity estimation device.

FIG. 9 illustrates a simplified diagram of a brain activity estimation device 10 according to an embodiment of the present invention. FIG. 10 illustrates a flowchart showing the flow of a process during identification of a component indicating a change of skin temperature that reflects brain function, in a brain activity estimation device 10.

The brain activity estimation device 10 is a device for estimating a human brain activity. As shown in FIG. 9, the brain activity estimation device 10 is equipped with a facial skin temperature acquisition element (means) 20 and a brain activity estimation element (means) 30.

The facial skin temperature acquisition means 20 detects the skin temperature of at least a part of the face of a person, and acquires a time series of facial skin temperature data that includes the detected temperature data and location data for the detected region (step S1). The facial skin temperature acquisition means 20 of the present embodiment is an infrared thermography device. As shown in FIG. 9 has an infrared camera 21 and a processing unit 22. The infrared camera 21 detects infrared emission energy emanating from the face of the person. In the present embodiment, the infrared camera 21 detects infrared emission energy emanating from the entire face of the person. The processing unit 22 converts the infrared emission energy detected by the infrared camera 21 to temperature as temperature data. The processing unit 22 creates a temperature distribution chart of the facial skin temperature of the entire face, in which the regions where the infrared emission energy was detected are used as location data (coordinate data). The processing unit 22 processes the created temperature distribution chart as facial skin temperature data corresponding to temperature conversion data. The facial skin temperature data corresponding to temperature conversion data is cumulated in a storage unit (not shown) of the processing unit 22.

In the present embodiment, the temperature distribution chart of the facial skin temperature data in the entire face is created in the processing unit 22, but no limitation is provided thereby; it would be acceptable to create a temperature distribution chart of facial skin temperature that includes at least the paranasal sinus peripheral region and/or the forehead, and to employ this data as facial skin temperature data corresponding to temperature conversion data.

In the present embodiment, the person is presented with a brain function-stimulating task for a given period, while the facial skin temperature data corresponding to temperature conversion data is being acquired by the facial skin temperature acquisition means 20. Specifically, the facial skin temperature data corresponding to temperature conversion data acquired by the facial skin temperature acquisition means 20 includes data for the period during which the person is being presented with a brain function-stimulating task. There are no particular limitations as to the brain function-stimulating task presented to the person, provided that the brain can be expected to be brought to a stimulated state thereby. The content thereof may be decided upon in an appropriate manner depending, for example, on the purpose for which the brain activity estimation device 10 is being utilized.

The brain activity estimation means 30 estimates a human brain activity on the basis of the facial skin temperature data corresponding to temperature conversion data that is acquired by the facial skin temperature acquisition means 20. Specifically, as shown in FIG. 9, the brain activity estimation means 30 has a conversion unit 31, an analysis unit 32, and an estimation unit 33.

The conversion unit 31 converts into relative temperature data the temperature data included in the facial skin temperature data corresponding to temperature conversion data, and creates facial skin temperature data based on the converted relative temperature data, i.e., facial skin temperature data corresponding to relative temperature conversion data (step S2). Specifically, the conversion unit 31 uses the average value of the temperature data that is included in facial skin temperature data corresponding to temperature conversion data captured at each of prescribed points in time (e.g., every 30 seconds) as a criterion value, and converts the temperature data to relative temperature data. The conversion unit 31 then utilizes the converted relative temperature data and location data to create facial skin temperature data corresponding to relative temperature conversion data.

The analysis unit 32 decomposes each of a time series of facial skin temperature data corresponding to temperature conversion data and the facial skin temperature data corresponding to relative temperature conversion data into a plurality of components by singular value decomposition principal component analysis, or independent component analysis (step S3). In the present embodiment, the analysis unit 32 carries out singular value decomposition for each the acquired facial skin temperature data corresponding to temperature conversion data and the converted facial skin temperature data corresponding to relative temperature conversion data, using the MATLAB (registered trademark)'s SVD as the analysis tool. Singular value decomposition is carried out on the acquired the time series of facial skin temperature data corresponding to temperature conversion data and facial skin temperature data corresponding to relative temperature conversion data, designating time data for each of prescribed (e.g., 30-second) periods as factors, and designating the facial skin temperature data corresponding to temperature conversion data and the facial skin temperature data corresponding to relative temperature conversion data in the periods as measures. Then, through singular value decomposition, the facial skin temperature data corresponding to temperature conversion data and the facial skin temperature data corresponding to relative temperature conversion data are decomposed into a plurality of components, and a temporal distribution, a spatial distribution, and a singular value indicating the magnitude of the components are calculated.

Additionally, in order to identify a component that indicates changes in skin temperature reflecting brain activity from among the plurality of components that are decomposed by singular value decomposition, the analysis unit 32 determines whether the components satisfy a first condition and a second condition (step S4a, step S4b, step S5a, and step S5b). In the present embodiment, the analysis unit 32 first determines whether components based on facial skin temperature data corresponding to temperature conversion data satisfy the first condition (step S4a). Then, for the component based on the facial skin temperature data corresponding to temperature conversion data and which in step S4a is determined to satisfy the first condition, the analysis unit 32 determines whether the component satisfies the second condition (step S4b). Then, of the components based on the facial skin temperature data corresponding to relative temperature conversion data, only for those components that match components determined in step S4a and step S4b to satisfy the first condition and the second condition, the analysis unit 32 determines whether those components satisfy the first condition (step S5a). Thereafter for the component based on facial skin temperature data corresponding to relative temperature conversion data determined in step S5a to satisfy the first condition, the analysis unit 32 determines whether the component satisfies the second condition (step S5b). However, the order in which determinations are made in the analysis unit 32 is not limited to that shown in the present embodiment; it would be acceptable, for example, that the analysis unit 32 respectively determines whether components based on facial skin temperature data corresponding to temperature conversion data, and components based on facial skin temperature data corresponding to relative temperature conversion data, satisfy the first condition and the second condition, and ultimately extracts components for which the determination results match.

The first condition is a condition to the effect that the amplitude of the component waveform of a component decomposed by singular value decomposition is correlated to changes when the brain is at rest and when the brain is stimulated. The analysis unit 32 extracts components that satisfy the first condition, as determination components from among the plurality of components. In the present embodiment, during the time that the facial skin temperature data corresponding to temperature conversion data is being acquired, there is a certain period for which the person is presented with a brain function-stimulating task. Designating periods in which the person is not presented with a brain function-stimulating task as times when the brain is at rest, and periods in which person is being presented with a brain function-stimulating task as times when the brain is stimulated, the analysis unit 32 performs a comparative analysis between component waveforms and periods in which brain function-stimulating tasks are presented, and periods when a brain function-stimulating task are not presented. Utilizing the results of the comparative analysis based on the component waveform data, the analysis unit 32 evaluates whether there is correlation between the waveforms of the components and times that the brain is at rest, and times that the brain is stimulated. The analysis unit 32 extracts those components evaluated as having correlation from among the plurality of components as determination components that satisfy the first condition. On the other hand, for components that among the plurality of components are those evaluated as lacking correlation, the analysis unit 32 determines that the components do not satisfy the first condition and are not components that indicate temperature changes reflecting a human brain activity (step S6).

In the present embodiment, during the time that the facial skin temperature data corresponding to temperature conversion data is being acquired, the person is presented with a brain function-stimulating task for a certain period, and the analysis unit 32 extracts determination components on the basis thereof; however, the content of the first condition, i.e., the means for extraction of determination components in the analysis unit 32, is not limited thereto. For example, in cases in which a component that has a component waveform having a correlation to times that the brain is at rest and times that the brain is stimulated has been identified from among a plurality of components beforehand through testing or the like, the analysis unit 32 may extract this component identified from among a plurality of components as a determination component. Also, in cases in which a human behavior known to be related to stimulation/rest of the brain, such as ocular motion or blinking, is detected in the brain activity estimation device, the analysis unit 32 may extract a determination component from among a plurality of components by conducting a comparative analysis and an evaluation for the detection result and the component waveforms of the components. The criterion by which the analysis unit 32 determines whether or not the first condition is met may be decided by simulation, testing, desktop calculation, or the like in an appropriate manner, depending on the purpose for which the brain activity estimation device 10 is being used.

The second condition is a condition that there are temperature changes in a prescribed region of the human face in the extracted determination components. The analysis unit 32 determines that components which are ones satisfying the second condition from among the determination components are components that are highly likely to be related to a human brain activity, and extracts these as candidate components. Specifically, on the basis of the presence or absence of temperature changes in a prescribed region of a human face, the analysis unit 32 determines whether the determination components are related to a human brain activity. In more specific terms, on the basis of temperature distribution data of the extracted determination components, the analysis unit 32 determines whether temperature changes are occurring in the paranasal sinus peripheral region and/or forehead. In cases in which such temperature changes are occurring, the analysis unit 32 determines that the determination components in question are components that meet the second condition and are highly likely to be related to a human brain activity, and extracts these as candidate components. On the other hand, in cases in which temperature changes are not occurring in the paranasal sinus peripheral region and/or forehead, the analysis unit 32 determines that the determination components in question are components that do not satisfy the second condition and are not indicative of changes in skin temperature reflecting brain activity (step S6). The criterion by which the analysis unit 32 determines whether or not the second condition is met may be decided by simulation, testing, desktop calculation, or the like in an appropriate manner, depending on the purpose for which the brain activity estimation device 10 is being used.

The analysis unit 32 then identifies the components that are determined to have met the second condition in step S5b to be components that indicate changes in skin temperature that reflect brain activity (step S7). Specifically, the components that is identified as components that indicate changes in skin temperature that reflect brain activity in step S7 can be said to be corresponding components between candidate components extracted by decomposing facial skin temperature data corresponding to temperature conversion data through singular value decomposition and analyzing it, and candidate components extracted by decomposing facial skin temperature data corresponding to relative temperature conversion data through singular value decomposition and analyzing it. Candidate components for which the two analyses do not match are determined to not be components that indicate temperature changes reflecting brain activity in step S6.

The estimation unit 33 estimates a human brain activity on the basis of components identified in the analysis unit 32 as being components that indicate skin temperature changes reflecting a human brain activity. In specific terms, on the basis of component waveform data of components identified by the analysis unit 32, the estimation unit 33 estimates whether the human brain was in an active state or the brain was not in an active state, at the time that the facial skin temperature data was acquired.

Through this configuration, a human brain activity can be estimated by this brain activity estimation device 10, on the basis of the skin temperature of the face. By having the estimation unit 33 display the estimate results on a display or the like, it can be discerned whether the person's brain is in an active state, or not in an active state.

In cases in which additional facial skin temperature data is acquired by the facial skin temperature acquisition means 20 after components that indicate changes in skin temperature reflecting brain activity have been identified by the analysis unit 32, the brain activity estimation device 10 may estimate whether the brain of the person in question is in the active state, or the brain is not in the active state at the time of acquisition of this facial skin temperature data, by decomposing the additional acquired facial skin temperature data into a plurality of components by singular value decomposition, and analyzing only the identified components. By utilizing this brain activity estimation device 10 to control equipment or appliances, such as an air conditioner or the like, an indoor environment can be close to the one suited to the person.

(5) Characteristics (5-1)

In cases in which data detected by any of the methods of electroencephalography, functional magnetic resonance imaging, or near infrared spectroscopy is utilized to estimate a human brain activity, either it has been necessary to use sensors that require preparatory processing, such as brain wave electrodes or probes, or the restrictions may arise as to the location of measurement. Additionally, the instruments used in these detection methods are extremely costly; therefore, attempts to manufacture brain activity detection devices outfitted with these instruments involve high manufacturing costs.

According to the present embodiment, a human brain activity is estimated on the basis of a time series of facial skin temperature data corresponding to temperature conversion data acquired by the facial skin temperature acquisition means 20. For this reason, a human brain activity can be estimated on the basis of the skin temperature of the face, even without the need to attach sensors that require preparatory processing, such as brain wave electrodes or probes. Consequently, a human brain activity can be estimated more easily than when electroencephalography, functional magnetic resonance imaging, near infrared spectroscopy, or other such conventional detection method is utilized.

According to the present embodiment, it is sufficient to be able to detect the skin temperature of at least part of the face, and therefore manufacturing costs can be kept lower than with brain activity estimation devices equipped with instruments that employ conventional detection methods.

Previous studies have taken an average-value approach, in which an average value was calculated for all of the temperature data included in a time series of facial skin temperature data acquired by the facial skin temperature acquisition means 20, and an analysis was carried on facial skin temperature data that was dependent on this calculated average, to estimate a human brain activity. However, facial skin temperature data included noise from sources that did not actually reflect brain activity, and as the effects of noise were relatively strong when temperature data for a part of a body was analyzed, brain activity could not be estimated accurately by the average-value approach.

As a result of painstaking research, the inventors conceived of a component-analytical approach, in which a time series of facial skin temperature data acquired by the facial skin temperature acquisition means 20 is decomposed into a plurality of components by singular value decomposition, principal component analysis, or independent component analysis, and components that are related to brain activity are identified from the decomposed plurality of components. With the component-analytical approach, all of the temperature data is decomposed, and therefore components that include noise can be eliminated, and brain activity can be estimated more accurately, as compared with the average-value approach.

Further, by utilizing the brain activity estimation device 10 of the present invention, medical diagnoses of conditions such as early onset of dementia can be made easily. Additionally, the brain activity estimation device 10 of the present invention can be utilized for evaluation of objective comfort, or applied in evaluating the effects of learning or objectively evaluating interests, and in lie detector devices or the like. Further, the brain activity estimation device can be utilized to evaluate drowsiness during driving of an automobile in the case where determination components can be extracted from among a plurality of components by the analysis unit 32 performing a comparative analysis and an evaluation to the waveforms of components and the detection results of a person's behavior which is known to be related to stimulation/rest of the brain, such as ocular motion or blinking.

(5-2)

In cases in which a person is actually presented or not presented with a brain function-stimulating task during acquisition of a time series of facial skin temperature data in order to create circumstances in which the person's brain is stimulated or at rest, components the waveforms of which correlates with times that the brain is stimulated and at rest may be said to have a high probability of indicating changes in skin temperature that are reflective of brain activity.

In the present embodiment, the person is presented with a brain function-stimulating task for a fixed period during the time that facial skin temperature data corresponding to temperature conversion data is being acquired by the facial skin temperature acquisition means 20. Specifically, in the present embodiment, circumstances in which the person's brain is stimulated or left at rest are created by either presenting or not presenting the person with a brain function-stimulating task. The facial skin temperature data thus acquired is then decomposed into a plurality of components by singular value decomposition. The component waveforms of the components and correlation thereof to times when the brain is stimulated and times when the brain is at rest are evaluated. Components that are determined to exhibit correlation are extracted as determination components from among the plurality of components. For this reason, the risk that components having a weak correlation to a human brain activity will be extracted as extraction components from among a plurality of components can be made lower than in cases where, for example, prescribed components specified in advance through testing or the like are extracted as extraction components from among a plurality of components.

(5-3)

There are instances in which the skin temperature of the face varies due to a person's face being contacted by cold or hot air from an air conditioner, by sunlight, or the like, so that the detected skin temperature of the face varies. If this happens, there is a risk that changes in facial skin temperature due to extrinsic factors unrelated to brain activity (noise) will become mixed into the facial skin temperature data.

In the present embodiment, facial skin temperature data corresponding to relative temperature conversion data based on temperature data which has been converted to relative temperature data from facial skin temperature data collected at each of prescribed points in time according to temperature conversion data is created. By creating the facial skin temperature data corresponding to relative temperature conversion data, relative changes in skin temperature of the face at each of the prescribed points in time can be tracked. Therefore, changes in facial skin temperature due to extrinsic factors unrelated to brain activity can be detected.

Moreover, in the present embodiment, besides the facial skin temperature data corresponding to temperature conversion data acquired by the facial skin temperature acquisition means 20, facial skin temperature data corresponding to relative temperature conversion data which is based on temperature data that has been converted to relative temperature data is decomposed into a plurality of components by singular value decomposition, and an analysis of each component is carried out. Therefore, components that include changes in facial skin temperature due to extrinsic factors unrelated to brain activity can be eliminated as noise components. In so doing, components that are related to a human brain activity can be accurately identified.

(5-4)

The facial skin temperature acquisition means 20 in the present embodiment is an infrared thermography device. For this reason, facial skin temperature data can be acquired in a state of no contact with the person being targeted, i.e., in a non-contact state. Consequently, the burden on the person being targeted can be made lower than when sensors are attached to the face and temperature data from the skin of the face is detected.

(5-5)

The brain has a mechanism called the selective brain cooling system, whereby the brain is cooled independently of body temperature. It is known that the selective brain cooling system uses the forehead and the paranasal sinus peripheral region to remove heat produced by brain activity. Thus, changes in facial skin temperature accompanying brain activity will appear in the forehead and/or paranasal sinus peripheral region (the glabella and paranasal peripheral region).

In the present embodiment, for determination components in which there is a correlation between the component waveform and a time when the brain is at rest or a time when the brain is stimulated, a determination is made as to whether a temperature change has occurred in the paranasal sinus peripheral region and/or forehead. In so doing, it can be accurately identified whether components extracted as determination components are components that are associated with a human brain activity.

(6) Modifications (6-1) Modification Example A

In the aforedescribed embodiment, the brain activity estimation means 30 has the conversion unit 31, and the facial skin temperature data corresponding to relative temperature conversion data is created by the conversion unit 31. Then, the analysis unit 32 subjects not only the facial skin temperature data corresponding to temperature conversion data which was acquired by the facial skin temperature acquisition means 20, but also the facial skin temperature data corresponding to relative temperature conversion data which is based on the temperature data that was converted to relative temperature data, to decomposition into a plurality of components by singular value decomposition, and carries out an analysis of the components.

Instead of this, the brain activity estimation means 30 may not have the conversion unit 31. In this case, it is possible to omit the process to create the facial skin temperature data corresponding to relative temperature conversion data, and the process to carry out analysis of the data based on the facial skin temperature data corresponding to relative temperature conversion data.

However, in order for components that are associated with a human brain activity to be identified accurately, it is preferable, as in the aforedescribed embodiment, that the brain activity estimation means 30 has the conversion unit 31, and the analysis unit 32 decomposes not only the facial skin temperature data corresponding to temperature conversion data which is acquired by the facial skin temperature acquisition means 20, but also the facial skin temperature data corresponding to relative temperature conversion data based on the temperature data that is converted to relative temperature data, into a plurality of components by singular value decomposition, and carries out an analysis of the components.

(6-2) Modification Example B

The facial skin temperature acquisition means 20 in the aforedescribed embodiment is an infrared thermography device which can acquire data from a target while in a state of non-contact therewith.

However, the facial skin temperature acquisition means is not limited to an infrared thermography device, provided that it is possible to detect skin temperature in at least part of the face of a person, and to acquire a time series of facial skin temperature data that includes the detected temperature data and location data of the detection region thereof.

For example, the facial skin temperature acquisition means may be a device that includes a temperature sensor. In specific terms, it would be acceptable to attach the temperature sensor to a prescribed region of a person's face, and to acquire a time series of facial skin temperature data on the basis of temperature data detected by the temperature sensor, and location data about the region where the temperature is attached. Thus, even in cases in which facial skin temperature data is acquired by a temperature sensor in a state of contact with a person being targeted, there is no need for processing before attaching the temperature sensor as with brain wave electrodes and the like, and therefore data can be acquired more easily than with cases in which electroencephalography, functional magnetic resonance imaging, near infrared spectroscopy, or other such conventional detection method is utilized. In so doing, the brain activity of a person can be estimated easily.

INDUSTRIAL APPLICABILITY

Because a human brain activity can be estimated easily, the present invention is effective for application to devices required to estimate a human brain activity.

What is claimed is:

1. A brain activity estimation device comprising:
a facial skin temperature acquisition element arranged and configured to detect a skin temperature of at least part of a human face, and to acquire facial skin temperature data including detected temperature data and location data of a detection region thereof in a time series manner; and
a brain activity estimation element arranged and configured to estimate human brain activity based on the facial skin temperature data acquired by the facial skin temperature acquisition element,
the brain activity estimation element being further arranged and configured to
decompose the facial skin temperature data into a plurality of components by singular value decomposition, principal component analysis, or independent component analysis,
extract a component as a determination component from among the plurality of components, the component having an amplitude of a component waveform thereof that is correlated to changes at a time when a brain is at rest and a time when a brain is stimulated, and
determine whether the determination component is related to the human brain activity based on a presence or absence of a temperature change in a prescribed region of the human face.

2. The brain activity estimation device according to claim 1, wherein
the facial skin temperature data includes data for a period in which the human is presented with a brain function-stimulating task, and
the brain activity estimation element is further arranged and configured to evaluate whether a correlation exists in the plurality of components by designating a period during which the person is not being presented with the brain function-stimulating task as the time when the brain is at rest, and by designating a period during which the person is being presented with the brain function-stimulating task as the time when the brain is being stimulated, and
the brain activity estimation element is further arranged and configured to extract a component evaluated as having the correlation as the determination component from among the plurality of components.

3. The brain activity estimation device according to claim 1, wherein
the brain activity estimation element is further arranged and configured to
create facial skin temperature data in which the temperature data included in the facial skin temperature data acquired at each of prescribed points in time is converted to relative temperature data, and
decompose each of the acquired facial skin temperature data and the created facial skin temperature data into a plurality of components by singular value decomposition, principal component analysis, or independent component analysis.

4. The brain activity estimation device according to claim 1, wherein
the facial skin temperature acquisition element includes an infrared thermography device.

5. The brain activity estimation device claim 1, wherein
the prescribed region includes at least one of a paranasal sinus peripheral region and a forehead.

6. A brain activity estimation method, comprising:
detecting a skin temperature in at least part of a human face, and acquiring facial skin temperature data that includes detected temperature data and location data of a detection region thereof in a time series manner; and
estimating human brain activity based on the facial skin temperature data acquired,
the estimating human brain activity including
decomposing the facial skin temperature data into a plurality of components by singular value decomposition, principal component analysis, or independent component analysis,
extracting a component as a determination component from among said plurality of components that were decomposed, the component having an amplitude of a component waveform thereof that is correlated to changes at a time when a brain is at rest and a time when a brain is stimulated, and
determining whether the determination component that is extracted is related to the human brain activity, based on a presence or absence of a temperature change in a prescribed region of the human face.

7. The brain activity estimation device according to claim 2, wherein
the brain activity estimation element is further arranged and configured to
create facial skin temperature data in which the temperature data included in the facial skin temperature data acquired at each of prescribed points in time is converted to relative temperature data, and
decompose each of the acquired facial skin temperature data and the created facial skin temperature data into a plurality of components by singular value decomposition, principal component analysis, or independent component analysis.

8. The brain activity estimation device according to claim 7, wherein
the facial skin temperature acquisition element includes an infrared thermography device.

9. The brain activity estimation device according to claim 8, wherein
the prescribed region includes at least one of a paranasal sinus peripheral region and a forehead.

10. The brain activity estimation device according to claim 2, wherein
the facial skin temperature acquisition element includes an infrared thermography device.

11. The brain activity estimation device according to claim 2, wherein
the prescribed region includes at least one of a paranasal sinus peripheral region and a forehead.

12. The brain activity estimation device according to claim 3, wherein
the facial skin temperature acquisition element includes an infrared thermography device.

13. The brain activity estimation device according to claim 3, wherein the prescribed region includes at least one of a paranasal sinus peripheral region and a forehead.

14. The brain activity estimation device according to claim 4, wherein
the prescribed region includes at least one of a paranasal sinus peripheral region and a forehead.

* * * * *